United States Patent [19]

Wentzel

[11] 4,384,471
[45] May 24, 1983

[54] CHROMATOGRAPHIC ANALYSIS OF HYDROCARBON MIXTURES

[75] Inventor: Clarence S. Wentzel, Parlin, N.J.

[73] Assignee: Engelhard Minerals & Chemicals Corporation, Menlo Park, N.J.

[21] Appl. No.: 214,911

[22] Filed: Dec. 10, 1980

[51] Int. Cl.³ .......................................... G01N 31/08
[52] U.S. Cl. ..................................... 73/23.1; 422/89; 436/140
[58] Field of Search ...................... 73/23.1; 55/67, 197, 55/386; 23/232 C; 422/89, 54; 436/140, 141, 139, 85, 161, 178

[56] References Cited

U.S. PATENT DOCUMENTS 3,550,428  12/1970  Mator et al. ......................... 73/23.1
4,287,752   9/1981  Ury ..................................... 73/23.1

OTHER PUBLICATIONS

L. Stavinoha et al., "Isolation and Determination of Aromatics in Gasoline by Gas Chrom.", *J. Chrom. Sci.*, vol. 10(9), pp. 583–589, 1972, vol. 79, No. 106597w.

G. Esposito et al., "Aromatic–Aliphatic selectivity of Cyanoethyl Liquid Phases", *J. Paint Tech.*, vol. 44(568), pp. 77–79, 1972, vol. 79, No. 76735.

Schulz et al., *27 Erdoel Kohle, Erdgas 25, Petrochem, Brennst-Chem.*, 345–352, 1974.

*Primary Examiner*—Stephen A. Kreitman
*Attorney, Agent, or Firm*—Inez L. Moselle

[57] ABSTRACT

The paraffin, olefin and aromatic compounds in a gasoline containing hydrocarbons up to about $C_{13}$ can be analyzed and identified by gas liquid chromatography. The aromatics are reversibly absorbed from the gasoline sample by N,N-bis(2-cyanoethyl) formamide while the olefins are irreversibly absorbed by sulfuric acid. Following separation by compound type, each group is resolved and identified by gas liquid chromatography.

20 Claims, 1 Drawing Figure

CHROMATOGRAPHIC ANALYSIS OF HYDROCARBON MIXTURES

BACKGROUND OF THE INVENTION

1. Field of the Invention

This invention relates to the analysis of complex mixtures of hydrocarbons. More particularly, it relates to the analysis of mixtures of paraffinic, olefinic and aromatic hydrocarbons by gas-liquid chromatography (GLC). It especially relates to the chromatographic analysis of gasolines.

2. Description of the Prior Art

In gas-liquid chromatography, a mobile phase, such as a gaseous stream of nitrogen or helium containing a mixture of solutes is passed over a stationary phase of a nonvolatile liquid which is evenly distributed as a thin layer on a noninteracting solid support. The stationary phase is most conveniently provided in a column. Each solute is translated down the column by the mobile phase alternately distributing itself between the two phases as it moves. The species become separated because the individual components travel at different rates through the column depending on their affinity for the gas and liquid phases. This affinity is referred to as the partition coefficient and is the ratio of the concentration of a species in the stationary (liquid) phase to its concentration in the mobile (gas) phase. The mixture is separated into its components, depending on the nature of the mixture and the immobile phase in the column, and passes from the column for analysis by a detector, typically a thermal conductivity detector or a flame ionization detector. The detector indicates and measures the amount of separated components in the carrier gas. The detector response is usually a series of peaks recorded as a function of time and constitutes a gas chromatogram. The time required for a component to pass through the column, or its retention time, is a qualitative factor, while the detector response, which can be measured as peak height or area can be related to concentration. The distance between two peaks indicating two components increases in proportion to the distance traveled and the width of the peak increases as the square root of the distance. Where the peaks are overlapping or resolution in the chromatographic column is insufficient between components with similar properties it is often useful to collect the effluent from the first column and inject it into a second chromatographic column employing a liquid phase with a different selectivity to provide more suitable conditions for the desired separation and analysis.

Analysis of gasoline by means of chromatography is known in the art. The procedures employed heretofore are often complex but nonetheless may be limited in the completeness of the analysis.

Schulz et al utilized several systems for analyzing olefin-containing gasolines so as to identify the paraffins, olefins and aromatics by gas chromatography. In one procedure, the olefins plus aromatics were reversibly absorbed in a pre-column of $AgNO_3$ on Sterchamol and the saturated gasoline portion was subjected to capillary gas chromatography. After the chromatogram of the paraffins was made, the pre-column was desorbed with a carrier gas to produce a chromatogram of the olefins and aromatics. However, this method did not permit complete identification where olefin isomers were very numerous. In another procedure used by Schulz et al, a capillary chromatogram was taken of the paraffins in a gasoline after the unsaturates (olefins and aromatics) were removed by sulfuric acid scrubbing in a pre-column. This analytical procedure was completed by use of another pre-column where the olefins, but not the aromatics, were selectively hydrogenated and the hydrogenated sample was analyzed to produce a second capillary chromatogram. Although this latter procedure yields a very accurate and complete analysis, it is very complex. (See 27 *Erdoel Kohle, Erdgas* 25, *Petrochem, Brennst-Chem.* 345-52 (1974).)

Block et al. employed a chromatographic analysis to determine the composition of a methanol-derived gasoline which had a maximum carbon number of $C_{11}$. In this procedure, the aromatics were reversibly absorbed in a pre-column followed by chromatographic analysis of the saturates and olefins remaining in the sample. The olefins were then removed from the sample in an absorber and the remaining saturates were resolved and analyzed in a chromatographic column. Following desorption by a carrier gas, the aromatics were chromatographically analyzed. The aromatic pre-cutter column was a wall coated open tubular (WCOT) column coated with a polar liquid phase of cyanopropyl phenyl silicone. The olefin absorber was mecuric perchlorate-perchloric acid (MP-PA) dispersed in a packed column. This absorber requires that the gas feed to the column have a precisely controlled water content. The two resolving columns employed were support coated open tubular (SCOT) columns using squalene as the coating in the aromatics column and squalane in the saturates and olefin resolving column. Three flame ionization detectors permitted simultaneous analysis of aromatics, saturates plus olefins and saturates. Although this procedure produced a detailed analysis, for the components analyzed, hydrocarbons heavier than $C_{10}$–$C_{11}$ were not analyzed. Further, the apparatus is extremely complex since it requires four ovens operating at different temperatures, two temperature programs, three flame ionization detectors and an effluent splitter for controlling temperature and pressure. In addition, the reversible aromatic absorber has a selectivity of $C_9$–$C_{11}$ which limits its effectiveness when analyzing higher boiling gasolines. Also, water vapor pressures can be a problem here. Traces of water vapor cause deterioration of the liquid phase aromatics absorber while the precise control required for the olefin absorber makes reproducibility a serious problem. It was for this latter reason that the ASTM abandoned development of this MP-PA column as a standard test. Overactivity of the MP-PA column can also undesirabily absorb branched paraffins and aromatics. (See, 15 *Chroma. Science* 504-12 (1977).)

British Pat. No. 1,146,250 discloses a method of gas-liquid chromatography analysis of hydrocarbon mixtures utilizing columns of different selectivity connected in series wherein one group of components, for example, aromatics, is separated in a first column containing a polar immobile liquid phase and another group, for example, paraffins, naphthenes and olefins, passes through the first column with a different speed and, without undergoing appreciable separation, finds more suitable conditions for separation in a second column which contains a non-polar immobile liquid phase. In one embodiment, the effluent from a preceding column is collected by freezing out this fraction in a U-tube packed with a filler material. This fraction is then injected into a following column by raising the temperature of the U-tube while the carrier gas is passed there-through. By utilizing a number of columns containing polar and non-polar immobile liquid phases and by collecting the several effluents for injection in a following column, the mixture is separated into its individual components for analysis by flame ionization detectors. Complete resolution and identification of a complex mixture of hydrocarbons required four chromatographic columns, two with a polar immobile liquid phase and two with a non-polar immobile liquid phase, and four U-tubes necessitating at least four freezing and heating operations resulting in the production of four chromatograms for a quantative analysis of a naphtha sample.

It is an object of this invention to chromatographically analyze the paraffin, olefin and aromatic components of a gasoline containing up to at least $C_{13}$ hydrocarbons with a minimum of equipment and analytical operations.

SUMMARY OF THE INVENTION

In accordance with the present invention it has been found that the paraffin, olefin and aromatic compounds in a gasoline containing hydrocarbons having a maximum carbon number of about $C_{13}$ can be analyzed and identified chromatographically. More particularly, this invention is directed to an apparatus and a method of performing chromatographic analysis on a gasoline.

In one embodiment the present invention is directed to a process for the gas-liquid chromatographic analysis of a hydrocarbon mixture containing paraffins, olefins and aromatics which comprises:

(a) passing a first vaporized sample comprising a hydrocarbon mixture containing paraffins, olefins and aromatics and a mobile gas phase in contact with an amount of N,N-bis (2-cyanoethyl) formamide effective to reversibly absorb the aromatics from said first vaporized sample producing a second vaporized sample comprising paraffins, olefins and the mobile gas phase, (b) chromatographically separating a portion of the second vaporized sample by passing said portion through a first gas-liquid chromatographic column, said column effective for chromatographically separating paraffins and olefins, (c) passing said chromatographically separated portion of the second vaporized sample in contact with a flame ionization detector to produce a chromatogram of said paraffins and olefins, (d) desorbing the aromatics from said formamide by contacting said formamide with a mobile gas phase to provide a third vaporized sample comprising aromatics and the mobile gas phase, (e) chromatographically separating the third vaporized sample by passing said third sample through a second gas-liquid chromatographic column, said column effective for chromatographically separating aromatics, (f) passing said chromatographically separated third vaporized sample in contact with the flame ionization detector to produce a chromatogram of said aromatics, (g) passing a second portion of said second vaporized sample in contact with an amount of sulfuric acid effective to irreversibly absorb the olefins from said second vaporized sample producing a fourth vaporized sample comprising paraffins and the mobile gas phase, (h) chromatographically separating the fourth vaporized sample by passing said fourth sample through a third gas-liquid chromatographic column effective for chromatographically separating paraffins, and (i) passing said chromatographically separated fourth vaporized sample in contact with the flame ionization detector to produce a chromatogram of said paraffins.

In another embodiment, this invention is directed to an improvement in the analysis of a hydrocarbon mixture containing paraffins, olefins and aromatics by gas-liquid chromatographic analysis of the type wherein the several types of hydrocarbons are separated by reversible or irreversible absorption, adsorption or chemical reaction and the effluent therefrom is chromatographically separated in a gas-liquid chromatographic column and analyzed, said improvement comprises:

(a) passing a vaporized sample of a hydrocarbon mixture comprising paraffins, olefins and aromatics in contact with an amount of N,N-bis-(2-cyanoethyl) formamide effective to reversibly absorb the aromatics from said mixture to produce a first effluent comprising paraffins and olefins, and (b) passing a portion of the first effluent in contact with an amount of sulfuric acid effective to irreversibly absorb the olefins from the first effluent to produce a second effluent comprising paraffins.

In still another embodiment, this invention is concerned with a gas-liquid chromatographic apparatus for analyzing the paraffins, olefins and aromatic composition of hydrocarbon mixtures which comprises:

(a) means for transporting a first vaporized sample comprising a hydrocarbon mixture comprising paraffins, olefins, and aromatics and a mobile gas phase to a first absorbing means, (b) a first absorbing means for reversibly absorbing aromatic compounds from said first vaporized sample to produce a second vaporized sample comprising paraffins and olefins, said first absorbing means comprising an amount of N,N-bis (2-cyanoethyl) formamide effective to reversibly absorb aromatic compounds, (c) means for transporting a portion of said second vaporized sample to a first chromatographic separation means, (d) a first gas-liquid chromatographic separation means for chromatographically separating paraffins and olefins, (e) detection means for detecting chromatographically separated paraffins, olefins and/or aromatics, and producing a chromatogram, (f) means for transporting chromatographically separated paraffins and olefins from said first chromatographic separation means to said detection means, (g) means for desorbing aromatic compounds from said first absorbing means to produce a third vaporized sample comprising aromatics and transporting said third vaporized sample to a second chromatographic separation means, (h) a second gas-liquid chromatographic separation means for chromatographically separating aromatics, (i) means for transporting chromatographically separated aromatics from said second chromatographic separation means to said detection means, (j) means for transporting a second portion of said second vaporized sample to a second absorbing means, (k) a second absorbing means for irreversibly absorbing olefins from a portion of the second vaporized sample to produce a fourth vaporized sample comprising paraffins, said second absorbing means comprising an amount of sulfuric acid effective to irreversibly absorb olefins, (l) means for transporting said fourth vaporized sample from said second absorbing means to a third chromatographic separation means, (m) a third gas-liquid chromatographic separation means for chromatographically separating paraffins, and (n) means for transporting chromatographically separated paraffins from said third chromatographic separation means to said detection means.

DESCRIPTION OF THE PREFERRED EMBODIMENTS

Figure 1:
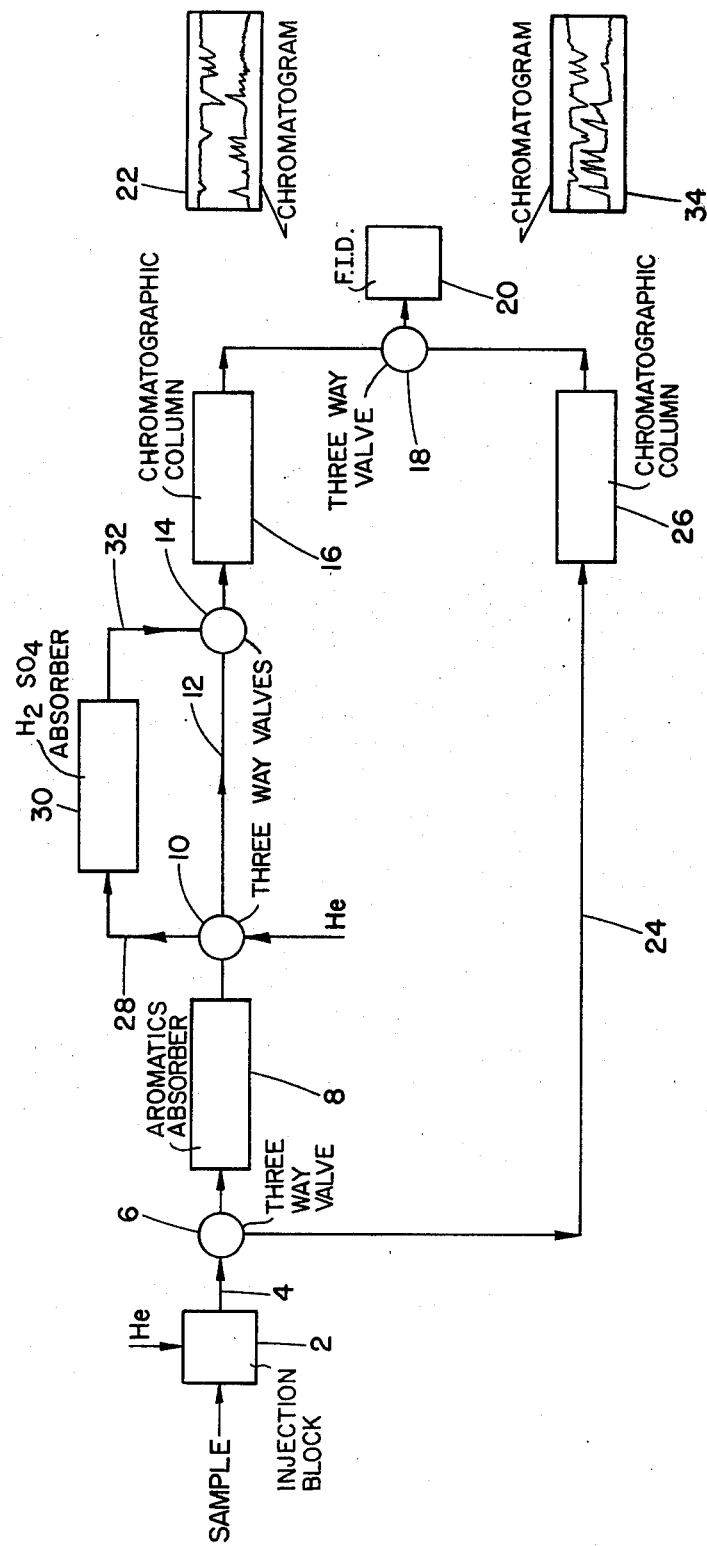
FIG. 1 is a schematic drawing of an apparatus utilized to practice this invention.

Broadly, it has been found that a gasoline containing paraffins, olefins and aromatics up to $C_{13}$ compounds can be separated into fractions, classified by type, and subsequently chromatographically analyzed to provide individual component separation and identification. Briefly, a particular organic compound, N,N-bis (2-cyanoethyl) formamide, reversibly absorbs aromatics up to about $C_{13}$ from a sample of gasoline. Subsequently, the sample, now depleted of its aromatic compounds, can be chromatographically separated and analyzed for its paraffin and olefin composition. The aromatics may then be desorbed and separated and analyzed by gas-liquid chromatographic equipment. A second sample may then be subjected to aromatic absorption by the N,N-bis (2-cyanoethyl) formamide followed by irreversible absorption of the olefins by sulfuric acid. The sample, now deplete of aromatics and olefins, is analyzed for paraffin composition by the gas-liquid chromatographic equipment. Any naphthenes present remain with and are analyzed together with the paraffins. This process produces chromatograms of the aromatics, the paraffins and the combined paraffins and olefins. From these chromatograms, the overall composition by hydrocarbon type may be obtained as well as the qualitative and quantitative analysis of the individual hydrocarbons. This is accomplished with two absorption columns, two wall coated open tubular (WCOT) chromatographic columns and one dual flame ionization detector all placed in two, or possibly one, programmable ovens. No pressure programming is required and neither is there need for an effluent splitter as with some other systems. The apparatus and process of this invention produce analytical data having a high degree of precision and reproducibility from a gasoline sample containing a complex mixture of hydrocarbons. The analysis is performed quickly and accurately by injecting two small quantities of the sample into the test equipment.

The process and equipment of this invention permits the separation and analysis of hydrocarbons containing up through thirteen carbon atoms by gas-liquid chromatography (GLC). This permits a complete analysis among the heavier portions of a gasoline which has not been possible by the GLC techniques employed heretofore. It is thought that the combination of the N,N-bis (2-cyanoethyl) formamide absorber which quantatively removes the aromatics from the gasoline and the sulfuric acid scrubber which selectivity removes only the olefins from the aromatic-depleted sample containing paraffins and olefins provides the degree of separation between hydrocarbon type up through $C_{13}$ not obtained in the prior art. Not only does the aromatics absorber perform its task at a high level of selectivity but the absorption is reversible so that the entire aromatic portion of the sample may subsequently be recovered for chromatographic analysis. The sulfuric acid absorber is so designed and operated that only the olefins are scrubbed from the paraffin-olefin stream (the aromatics having been removed in the upstream aromatics absorber). Although sulfuric acid under certain conditions will scrub branched paraffins from a hydrocarbon mixture, the design and operating conditions employed in the present invention prevent any paraffin absorption in this sulfuric acid absorber.

Referring to FIG. 1, the process and apparatus of the present invention may be described as follows: A sample of the gasoline-type hydrocarbon mixtures under test is injected by means of a syringe into heated injection block 2. The gasoline-type hydrocarbon mixtures which may be analyzed by the process and apparatus of this invention are generally referred to as gasolines or naphthas. There may be refined, partly refined or unrefined liquid petroleum products, generally having a boiling range of about 100°–450° F. Typical examples of these materials are straight run naphtha (obtained from atmospheric distillation of crude oil), thermally cracked naphtha, catalytically cracked naphtha, motor gasolines and the like and will be referred to herein collectively as gasolines. The gasolines are complex mixtures of hydrocarbons which can broadly be classified as containing paraffins, naphthenes, olefins and aromatics up to about $C_{13}$ hydrocarbons. In the separations effected in this invention three broad separations are made—aromatics, olefins and paraffins—with the naphthenes being collected with the paraffins. The quantity of the sample is usually about 0.1 to 5 microliter ($\mu$l). A stream of inert gas is provided as the mobile phase for the gas-liquid chromatography. Among the inert gases which may be employed are nitrogen, argon or helium with helium being preferred and which will serve as the mobile phase in this description. As the gasoline sample is vaporized by heated injection block 2, a stream of helium is introduced therein and carries the vaporized sample through line 4 and three way valve 6 which has been previously set to direct the test sample to aromatics absorber column 8. This column is a packed column containing N,N-bis (2-cyanoethyl) formamide dispersed on an inert support. It has been found that N,N-bis(2-cyanoethyl)formamide will selectively absorb aromatic hydrocarbons up to $C_{13}$ leaving the paraffins and olefins in the gasoline unabsorbed. Not only are the aromatics selectively absorbed but they are reversibly absorbed, i.e., they may be quantatively desorbed by a reverse flow of the mobile phase. This particular formamide has the unique property of selectively absorbing aromatics, i.e. all nonaromatics up to $C_{13}$ will pass from the aromatics absorber before benzene. Typically, column 8 is a small diameter column containing a sufficient quantity of the formamide to absorb the aromatics from the sample. The inert support may be any of the well known supports used in chromatography including diatomaceous earth, fire brick, kieselguhr and the like. In a preferred embodiment the N,N-bis-(2-cyanoethyl)formamide is dispersed on diatomaceous earth in a 3 foot long column having a 0.25 inch internal diameter. The aromatics absorber column is operated isothermally during both absorption and desorption at 90°–150° C., preferably 95°–115° C. and most preferably about 100° C.

As the sample flows through column 8 the aromatics are selectively absorbed leaving the aromatics and olefins which are carried from column 8 by the flow of helium through four-way valve 10 which is set to direct the remaining sample through line 12 and three-way valve 14 which in turn is positioned so as to permit the sample to enter chromatographic column 16. This column is a capillary column containing a stationary liquid with sufficient resolving power to chromatographically separate the paraffins and olefins in the gasoline sample. Gas-liquid chromatographic equipment to perform the desired separation and analysis is known in the art and may be employed here. Typical of the equipment which may be usefully employed in this invention is a wall coated open tubular (WCOT) chromatographic column employing a non-polar liquid as the immobile phase. A 0.01 in I.D. column, 200 feet long, employing squalane as the stationary liquid, has proven useful in the present invention. A programmed temperature cycle ranging from $-20°$ to $100°$ C. may be employed. Holding the temperature at $-20°$ C. for eight minutes followed by a $1°$ C. increase per minute is one particular program which has proven useful. As the parafins and olefins pass through the column they are chromatographically separated. As the separated components are eluted from column 16 they are directed by three-way valve 18 to a detector for identification and preparation of a chromatogram. Any of the conventional detector means may be employed here, such as a flame ionization detector (FID) or a thermal conductivity detector. In the present invention a flame ionization detector has been found useful. The separated olefins and paraffins pass to flame ionization detector 20 where the individual components are identified both qualatatively and quantatively on chromatogram 22.

The aromatics absorbed by the N,N-bis-(2-cyanoethyl)formamide are then desorbed for chromatographic analysis. Aromatics absorber 8 is desorbed by a reverse flow of helium which is introduced into absorber 8 through four way valve 10. During desorption, no change in temperatue is necessary to effect the desorption of the aromatics so that the temperature employed during absorption may be maintained for desorption. Reverse flow is required to obtain complete desorption. The $C_{10}$-$C_{13}$ aromatics will not desorb at about $100°$ C. unless reverse flow is employed. As the desorbed aromatics exit from aromatic absorber 8 they pass through three way valve 6 which is positioned to direct the flow to chromatographic column 26. This column is a capillary column containing a stationary liquid with sufficient resolving power to chromatographically separate the aromatics of a gasoline sample. GLC equipment to perform the desired separation is known in the art and may be employed here. It has been found that the WCOT column employing squalane (0.01 in. I D$\times$200 feet long) temperature programmed from $-20°$ to $100°$ C. usefully employed as chromatographic column 16 may be duplicated and serve as chromatographic column 26. The aromatics flow through column 26 where they are chromatographically separated. As they pass from column 26, they flow through three-way valve 18, positioned to direct the separated aromatics to flame ionization detector 20. As the aromatics pass through FID 20 the individual components are identified as a response recorded on chromatogram 22. In this fashion two series of peaks are formed on chromatogram 22, one for the combined stream of paraffins and olefins and the other for the aromatics.

A second sample is then injected into heated injection block 2. In a fashion similar to that described above, the vaporized sample is carried by a stream of helium through line 4, three way valve 6 and aromatics absorber 8 where the aromatics are removed from the sample. The remaining paraffins and olefins then flow through three way valve 10, which has been positioned to direct the flow to line 28. The stream flows through line 28 to sulfuric acid absorber 30. The purpose of this absorber is to remove only the olefins from the remaining sample so that the paraffins (including naphthenes) can be identified. Although sulfuric acid is known for its ability to scrub olefins from a gas stream, it is also sufficiently active under certain conditions to remove branched chain paraffins as well. It has been found that a sulfuric acid scrubber can be designed and operated so as to scrub only the olefins from this stream leaving the straight chain and branched chain paraffins (and naphthenes) in the helium stream. The sulfuric acid is present in a packed column in an amount effective to remove olefins but not branched chain paraffins from a gasoline sample. One means of achieving this is to disperse the sulfuric acid on an inert support having a low surface area, typically a support in a 30–50 mesh particle size. Useful supports include such materials as diatomaceous earth, fire brick, kieselguhr and the like with diatomaceous earth being preferred. The sulfuric acid should constitute about 35–45% of the combined weight of the acid and the support. It has been found that a small volume of the supported sulfuric acid will effectively remove only the olefins if the temperature is precisely controlled at about $100°$ C.$\pm 5°$ C. For example, a packed column 0.25"I.D. by only 2.5" long when used in conjunction with the aromatics absorber and chromatographic columns as described herein will effectively perform in the required fashion when controlled to about $100°$ C. Surprisingly, this extremely short column performs very effectively contrary to what one skilled in the gas chromatographic art might expect. Of course, where apparatus having dimensions and/or capabilities other than that exemplified herein is employed, some preliminary experimentation may be required to obtain the optimum design and operation of the several columns for the desired analysis but it is apparent that this will not require an undue amount of experimentation for the skilled artisan. Although it is usual practice, in preparing liquid phase chromatographic columns, to dry the wetted inert supports, it has been found that the inert supports wetted with sulfuric acid can be employed per se, i.e. without drying them. It is not known if this contributes to the effectiveness of the very small acid scrubber but it is known that the acid wetted supports provide effective removal of the olefins.

As the stream of paraffins and olefins passes through sulfuric acid absorber 30, the olefins are selectively removed. The remaining paraffins exit through line 32 and pass through three way valve 14, positioned to direct the flow to chromatographic column 16. The paraffins flow through column 16 is the same fashion as the combined stream of olefins and paraffins passed through this same column in the above description. Column 16 is operated in the same fashion as for the olefins and paraffins. As the paraffins pass through the WCOT column, they are chromatographically separated. When the separated paraffins pass from column 16 they are directed by three way valve 18 to FID 20 for identification and the preparation of a chromatogram. Chromatogram 34 is prepared on which the identification of the paraffins is indicated as a series of peaks.

In the same fashion as described above, the aromatics absorbed in aromatics absorber 8 are desorbed by a reverse flow of helium. Then they are chromatographically separated in chromatographic column 26, identified by FID 20 and the response thereto is recorded on chromatogram 34. Two series of peaks are formed on chromatogram 34, one for the paraffins present in the gasoline and the other for the aromatics.

The apparatus of this invention may conveniently be located in two ovens. The first oven is operated isothermally at a preferred temperature range of 95°-115° C. and contains the aromatics absorber and the sulfuric acid absorber. The second oven contains the chromatographic columns. This oven is provided with a temperature programmer so that the column temperature may be varied through a cycle to provide the desired degree of separation. One cycle which has proven successful is to maintain −20° C. for about eight minutes followed by a 1° C. increase per minute to a maximum temperature of 100° C. Those skilled in the art can appreciate that where convenient, two ovens, one isothermal and one programmable, can be employed in one instrument. The oven and programming equipment are well known in the field and are readily obtainable commercially.

All parts and percentages expressed herein are by weight unless indicated to the contrary.

The following examples will serve to illustrate the subject invention.

EXAMPLE I

A synthetic blend of hydrocarbons was prepared to evaluate the process and apparatus of the present invention. The blend consisted of 32 individual hydrocarbons and contained n-paraffins, branched paraffins, olefins and aromatics. The blend had the following composition:

|  | Wt. % |
|---|---|
| Saturates | 52.9 |
| Olefins | 24.9 |
| Aromatics | 22.2 |
|  | 100.0 |

This synthetic blend was analyzed as follows:

Referring to FIG. 1 which graphically depicts a simplified flow plan of the invention, 0.1 to 5 microliters of a sample of the synthetic hydrocarbon blend were injected by means of a syringe into the injection port of heated injection block 2 where the sample was vaporized. A continuous stream of helium introduced into heated injection block 2 carried the vaporized sample along line 4 and through three-way valve 6 to aromatic absorber column 8. This column was a packed column, 0.25 inches I.D.×3 feet, containing N,N-bis(2-cyanoethyl)foramide (CEF) dispersed on an inert support of diatomaceous earth, available under the tradename Chromosorb P or Chromosorb W. As the sample passed through this column, which was maintained at a temperature of about 100° C. the CEF selectively absorbed the aromatics from the hydrocarbon sample. The remaining sample of saturates and olefins passed from column 8 through four-way valve 10 which was positioned to direct the sample to line 12 and three way valve 14 which in turn was positioned so as to permit the sample to enter chromatographic column 16. This column was a capillary column with sufficient resolving power to separate paraffins and olefins whose boiling points are in the gasoline boiling range, e.g. $C_5$–$C_{13}$ hydrocarbons. Column 16 was 0.01 inches I.D.×200 feet and was a wall coated open tubular (WCOT) column coated with squalane. The squalane effected a chromatographic separation of the saturated and olefinic hydrocarbons. As the hydrocarbons passed from column 16, three way valve 18 directed them to dual flame ionization detector (FID) 20 where chromatogram 22 of the saturates and olefins was obtained.

A chromatogram of the aromatics adsorbed in column 8 was then obtained on chromatogram 22 as follows: Helium was introduced through four way valve 10 to desorb column 8 with a reverse flow of gas. The column was still being maintained at about 100° C. Three way valves 6 and 18 were positioned to direct the desorbed aromatics through line 24 and chromatographic column 26 for the chromatographic separation and the subsequent preparation of a chromatogram of the aromatic portion of the synthetic blend on chromatogram 22 as it passed through FID 20. Column 26 was a duplicate of WCOT column 16 in that it was also 0.01 inches I.D.×200 feet and was coated with squalane.

To complete the analysis, a second sample of the synthetic blend was injected into heated injection block 2 after three way valve 6, four way valve 10 and three way valve 14 were positioned to permit the sample to be directed to aromatic absorber column 8, olefin absorber column 30 and chromatographic column 16. The stream of helium carried the vaporized sample of the synthetic blend from heated injection block 2 through line 4 and valve 6 to aromatic absorber column 8 where the CEF again selectively adsorbed the aromatic hydrocarbons from the sample. The saturates and olefins then passed from column 8 through four way valve 10, and line 28 into olefin absorber column 30. This column was a packed column, 0.25 inches I.D×2.5 inches long, containing concentrated sulfuric acid dispersed on an inert support of diatomaceous earth, available under the tradename Chromosorb P. The sulfuric acid constituted about 40% of the combined weight of the acid and the support. As the saturates and olefins passed through column 30 which was maintained at temperature of about 100° C., the olefins were selectively and irreversibly scrubbed from the gas stream by the sulfuric acid. The sample, now depleted of aromatics and olefins, was passed through three way valve 14 and chromatographic column 16 where the saturates were separated for subsequent analysis by FID 20 and the preparation of chromatogram 34.

In a fashion similar to that described above, the aromatics were desorbed from column 8, chromatographically separated in column 26 and analyzed by FID 20 for the preparation of the aromatics chromatogram on chromatogram 34.

Two chromatograms were prepared. Chromatogram 22 contained two chromatograms, one of the combined paraffins and olefins and the second of the aromatics. The two chromatograms on chromatogram 34 were of the paraffins alone and the aromatics.

Four separate runs were made. The data obtained from the chromatograms is presented in Table I below.

TABLE I

REPRODUCIBILITY DATA
SYNTHETIC BLEND
HYDROCARBON TYPE ANALYSIS
WT %

|  | Saturates | Olefins | Aromatics |
|---|---|---|---|
| Run 1 | 52.4 | 24.8 | 22.8 |
| Run 2 | 52.5 | 25.4 | 22.2 |
| Run 3 | 53.1 | 24.5 | 22.4 |
| Run 4 | 52.3 | 25.5 | 22.2 |
| Mean | 52.57 | 25.05 | 22.4 |
| Stand Dev. | 0.36 | 0.48 | 0.28 |
| Rel. Dev. | 0.007 | 0.019 | 0.013 |
| True Blend Values | 52.9 | 24.9 | 22.2 |

NOTE*
Synthetic blend contains 32 components; n-paraffins, branched paraffins, olefins and aromatics.

The reproducibility was excellent. The results obtained are in excellent agreement with the true values. In fact, the agreement is significantly better than the published precision for the ASTM-D1319 standard test for hydrocarbon types.

EXAMPLE II

A sample of a fluid catalytically cracked gasoline was analyzed in the fashion of Example I using the same equipment.

The first strip chart obtained on this gasoline sample contained the chromatograms of the aromatic portion and the combined saturates and olefin portion of the sample. The second strip chart contained the chromatograms obtained when the olefins were removed from the sample by sulfuric acid scrubbing. On this second strip chart, one chromatogram was of the aromatics and the other was of the saturates. The peaks on the chromatograms were numerically identified employing the system utilized by Sanders and Maynard and published in 40 *Analytical Chemistry* 527, 531-32 (March 1968). Thus, peaks 40 and 75 on the chromatogram of the aromatics represented benzene and toluene, respectively, and peaks 25 and 150 on the chromatogram of the saturates represented 2-methylpentane and n-decane, respectively.

The hydrocarbon type analysis and the individual component analysis obtained from these chromatograms are presented in Tables II and III below.

TABLE II

REPRODUCIBILITY DATA
FLUID CAT. CRACKED GASOLINE
HYDROCARBON TYPE ANALYSIS
WT %

|  | Saturates | Olefins | Aromatics |
|---|---|---|---|
| Run 1 | 37.0 | 29.6 | 33.4 |
| Run 2 | 36.6 | 30.7 | 32.7 |
| Run 3 | 37.4 | 29.9 | 32.7 |
| Run 4 | 36.2 | 31.2 | 32.6 |
| Mean | 36.80 | 30.35 | 32.85 |
| Stand. Dev. | 0.51 | 0.73 | 0.37 |
| Rel. Dev. | 0.014 | 0.024 | 0.011 |

TABLE III

REPRODUCIBILITY DATA
FLUID CAT. CRACKED GASOLINE
INDIVIDUAL COMPONENT ANALYSIS
WT %

|  | Run 1 | Run 2 | Run 3 | Run 4 |
|---|---|---|---|---|
| Isopentane | 1.09 | 1.15 | 1.13 | 1.11 |
| n-Pentane | 0.16 | 0.16 | 0.16 | 0.16 |
| Cyclopentane | 0.05 | 0.05 | 0.05 | 0.05 |
| 2,3 Dimethylbutane | 0.83 | 0.84 | 0.83 | 0.82 |
| 2-Methylpentane | 3.61 | 3.60 | 3.62 | 3.58 |
| 3-Methylpentane | 3.67 | 3.58 | 3.60 | 3.56 |
| n-Hexane | 0.54 | 0.53 | 0.53 | 0.53 |
| Methylcyclopentane | 1.76 | 1.73 | 1.75 | 1.73 |
| 2,4 Dimethylpentane | 0.40 | 0.40 | 0.40 | 0.39 |
| Cyclohexane | 0.10 | 0.09 | 0.09 | 0.09 |
| 2-Methylhexane | 2.11 | 2.11 | 2.13 | 2.07 |
| 2,3 Dimethylpentane | 0.60 | 0.59 | 0.60 | 0.59 |
| 3-Methylhexane | 2.58 | 2.55 | 2.59 | 2.53 |
| 1-cis-3 Dimethylcyclopentane | 0.63 | 0.61 | 0.62 | 0.61 |
| 1-trans-3 Dimethylcyclopentane | 0.33 | 0.33 | 0.33 | 0.32 |
| 3 Ethylpentane | 0.13 | 0.13 | 0.13 | 0.13 |
| n-Heptane | 0.38 | 0.37 | 0.38 | 0.36 |
| 1-cis-2 Dimethylcyclopentane | 0.46 | 0.46 | 0.47 | 0.46 |
| Methylcyclohexane | 0.98 | 0.98 | 0.99 | 0.97 |
| 2,5 Dimethylhexane | 0.38 | 0.38 | 0.38 | 0.37 |
| 2,4 Dimethylhexane | 0.29 | 0.30 | 0.30 | 0.29 |
| 1-t-2-c-4 Trimethylcyclopentane | 0.30 | 0.29 | 0.30 | 0.29 |
| 1-t-2-c-3 Trimethylcyclopentane | 0.10 | 0.10 | 0.10 | 0.10 |
| 2,3 Dimethylhexane | 0.23 | 0.23 | 0.24 | 0.23 |
| 2, Methylheptane | 1.04 | 1.04 | 1.05 | 1.02 |
| 4 Methylheptane | 0.45 | 0.45 | 0.46 | 0.45 |
| 3,4 Dimethylhexane | 0.16 | 0.16 | 0.17 | 0.16 |
| 3 Methylheptane | 1.35 | 1.35 | 1.37 | 1.32 |
| n-Octane | 0.39 | 0.39 | 0.40 | 0.38 |
| 2,3,5 Trimethylhexane | 0.16 | 0.16 | 0.16 | 0.16 |
| 2,4 Dimethyl-3-ethylpentane | 0.42 | 0.43 | 0.43 | 0.43 |
| 2,3 Dimethylheptane | 0.14 | 0.13 | 0.14 | 0.13 |
| 3,4 Dimethylheptane | 0.24 | 0.24 | 0.25 | 0.24 |
| 4 Methyloctane | 0.44 | 0.44 | 0.45 | 0.43 |
| 2 Methyloctane | 0.56 | 0.56 | 0.57 | 0.55 |
| 2,2,4 Trimethylheptane | 0.58 | 0.58 | 0.59 | 0.57 |
| n-Nonane | 0.21 | 0.20 | 0.21 | 0.20 |
| n-Decane | 0.09 | 0.09 | 0.10 | 0.09 |
| n-Undecane | 0.09 | 0.09 | 0.09 | 0.09 |
| n-Dodecane | 0.11 | 0.11 | 0.11 | 0.10 |
| Benzene | 2.11 | 2.06 | 1.98 | 1.94 |
| Toluene | 2.79 | 2.75 | 2.80 | 2.70 |
| Ethylbenzene | 0.88 | 0.87 | 0.90 | 0.87 |
| p-Xylene | 1.09 | 1.08 | 1.10 | 1.10 |
| m-Xylene | 3.50 | 3.43 | 3.44 | 3.42 |
| o-Xylene | 1.61 | 1.58 | 1.57 | 1.60 |
| Isopropylbenzene | 0.05 | 0.04 | 0.04 | 0.04 |
| n-Propylbenzene | 0.34 | 0.32 | 0.31 | 0.32 |
| 1-Methyl-3-Ethylbenzene | 1.87 | 1.83 | 1.82 | 1.85 |
| 1-Methyl-4-Ethylbenzene | 0.62 | 0.60 | 0.60 | 0.60 |
| 1-Methyl-2-Ethylbenzene | 0.53 | 0.52 | 0.52 | 0.53 |
| 1,3,5 Trimethylbenzene | 0.99 | 0.97 | 0.97 | 0.99 |
| 1,2,4 Trimethylbenzene | 3.32 | 3.23 | 3.25 | 3.25 |
| 1,2,3 Trimethylbenzene | 0.99 | 0.97 | 0.96 | 0.98 |
| 1-Methyl-2-isopropylbenzene | 0.42 | 0.41 | 0.42 | 0.40 |
| 1,3 Diethylbenzene | 0.23 | 0.24 | 0.25 | 0.24 |
| 1-Methyl-3-n-propylbenzene | 0.58 | 0.56 | 0.56 | 0.58 |
| n-Butylbenzene | 0.14 | 0.14 | 0.14 | 0.15 |
| 1,2 Diethylbenzene | 0.32 | 0.32 | 0.32 | 0.33 |
| 1-Methyl-2-n-propylbenzene | 0.17 | 0.16 | 0.16 | 0.17 |
| 1,3 Dimethyl-5-ethylbenzene | 0.69 | 0.67 | 0.66 | 0.67 |
| 1,4 Dimethyl-2-ethylbenzene | 0.92 | 0.91 | 0.91 | 0.91 |
| 1,3 Dimethyl-4-ethylbenzene | 0.40 | 0.40 | 0.40 | 0.40 |
| 1,3 Dimethyl-2-ethylbenzene | 0.80 | 0.79 | 0.80 | 0.79 |
| 1,2 Dimethyl-3-ethylbenzene | 0.16 | 0.16 | 0.16 | 0.16 |
| 1,2,4,5 Tetramethylbenzene | 0.51 | 0.50 | 0.50 | 0.51 |
| 1,2,3,5 Tetramethylbenzene | 0.72 | 0.70 | 0.69 | 0.70 |

These data show that the method of this invention produces analytical data with a precision significantly better than that obtained by the "FIA" analysis of ASTM-D 1319.

What is claimed is:

1. A process for the gas-liquid chromatographic analysis of a hydrocarbon mixture containing paraffins, olefins and aromatics which comprises:
   (a) passing a first vaporized sample comprising a hydrocarbon mixture containing paraffins, olefins and aromatics and a mobile gas phase in contact with an amount of N,N-bis(2-cyanoethyl)formamide effective to reversibly absorb the aromatics from said first vaporized sample producing a second vaporized sample comprising paraffins, olefins and the mobile gas phase,
   (b) chromotographically separating a portion of the second vaporized sample by passing said portion through a first gas-liquid chromatographic column, said column effective for chromatographically separating paraffins and olefins,
   (c) passing said chromatographically separated portion of the second vaporized sample in contact with a flame ionization detector to produce a chromatogram of said paraffins and olefins,
   (d) desorbing the aromatics from said formamide by contacting said formamide with a mobile gas phase to provide a third vaporized sample comprising aromatics and the mobile gas phase,
   (e) chromatographically separating the third vaporized sample by passing said third sample through a second gas-liquid chromatographic column, said column effective for chromatographically separating aromatics,
   (f) passing said chromatographically separated third vaporized sample in contact with the flame ionization detector to produce a chromatogram of said aromatics,
   (g) passing a second portion of said second vaporized sample in contact with an amount of sulfuric acid effective to irreversibly absorb the olefins from said second vaporized sample producing a fourth vaporized sample comprising paraffins and the mobile gas phase,
   (h) chromatographically separating the fourth vaporized sample by passing said fourth sample through a third gas-liquid chromatographic column effective for chromatographically separating paraffins, and
   (i) passing said chromatographically separated fourth vaporized sample in contact with the flame ionization detector to produce a chromatogram of said paraffins.

2. A process according to claim 1 wherein the mobile gas phase is helium.

3. A process according to claim 1 wherein the first, second, and third gas-liquid chromatographic columns are wall coated open tubular columns, said coating comprising squalane.

4. A process according to claim 3 wherein the first chromatographic column also serves as the third chromatographic column.

5. A process according to claim 1 wherein the N,N-bis(2-cyanoethyl)formamide is dispersed on an inert support.

6. A process according to claim 1 wherein the sulfuric acid is dispersed on an inert support.

7. A process according to claim 1 wherein the hydrocarbon mixture is a gasoline containing up to at least $C_{13}$ hydrocarbons.

8. A process according to claim 1 wherein steps (a) and (d) are each conducted at a temperature of 95°–115° C., steps (b), (e) and (h) are each conducted at a programmed temperature in the range of −20° to +100° C., and step (g) is conducted at a temperature of 100° C.±5° C.

9. A process according to claim 1 wherein the desorption of step (d) is effected with a reverse flow of the mobile gas phase.

10. In the analysis of a hydrocarbon mixture containing paraffins, olefins and aromatics by gas-liquid chromatographic analysis of the type wherein the several types of hydrocarbons are separated by reversible or irreversible absorption, adsorption or chemical reaction and the effluent therefrom is chromatographically separated in a gas-liquid chromatographic column and analyzed, the improvement which comprises:
   (a) passing a vaporized sample of a hydrocarbon mixture comprising paraffins, olefins and aromatics in contact with an amount of N,N-bis-(2-cyanoethyl)-formamide effective to reversibly absorb the aromatics from said mixture to product a first effluent comprising paraffins and olefins, and
   (b) passing a portion of the first effluent in contact with an amount of sulfuric acid effective to irreversibly absorb the olefins from the first effluent to produce a second effluent comprising paraffins.

11. The improvement according to claim 10 including the following additional step:
   (c) desorbing the aromatics from the formamide by contacting said formamide with a reverse flow of an inert gas to produce a third effluent comprising aromatics.

12. The improvement according to claim 10 wherein step (a) is conducted at a temperature of 95°–115° C. and step (b) is conducted at a temperature of 100°±5° C.

13. The improvement according to claim 11 wherein step (c) is conducted at a temperature of 95°–115° C.

14. A gas-liquid chromatographic apparatus for analyzing the paraffinic, olefinic and aromatic composition of hydrocarbon mixtures comprising:
   (a) means for transporting a first vaporized sample comprising a hydrocarbon mixture comprising paraffins, olefins, and aromatics and a mobile gas phase to a first absorbing means,
   (b) a first absorbing means for reversibly absorbing aromatic compounds from said first vaporized sample to produce a second vaporized sample comprising paraffins and olefins, said first absorbing means comprising an amount of N,N-bis(2-cyanoethyl)-formamide effective to reversibly absorb aromatic compounds,
   (c) means for transporting a portion of said second vaporized sample to a first chromatographic separation means,
   (d) a first gas-liquid chromatographic separation means for chromatographically separating paraffins and olefins,
   (e) detection means for detecting chromatographically separated paraffins, olefins and/or aromatics, and producing a chromatogram,
   (f) means for transporting chromatographically separated paraffins and olefins from said first chromatographic separation means to said detection means,
   (g) means for desorbing aromatic compounds from said first absorbing means to produce a third vaporized sample comprising aromatics and transporting said third vaporized sample to a second chromatographic separation means, (h) a second gas-liquid chromatographic separation means for chromatographically separating aromatics, (i) means for transporting chromatographically separated aromatics from said second chromatographic separation means to said detection means, (j) means for transporting a second portion of said second vaporized sample to a second absorbing means, (k) a second absorbing means for irreversibly absorbing olefins from a portion of the second vaporized sample to produce a fourth vaporized sample comprising paraffins, said second absorbing means comprising an amount of sulfuric acid effective to irreversibly absorb olefins, (l) means for transporting said fourth vaporized sample from said second absorbing means to a third chromatographic separation means, (m) a third gas-liquid chromatographic separation means for chromatographically separating paraffins, and (n) means for transporting chromatographically separated paraffins from said third chromatographic separation means to said detection means.

15. An apparatus according to claim 14 wherein the first, second and third gas-liquid chromatographic separation means each comprises a wall coated open tubular column, said coating comprising squalane.

16. An apparatus according to claim 15 wherein the first chromatographic means also serves as the third chromatographic means and the transporting means of element (f) also serves as the transporting means of element (n).

17. An apparatus according to claim 14 wherein the detection means comprises a flame ionization detector.

18. An apparatus according to claim 14 wherein the N,N-bis(2-cyanoethyl)formamide of the first absorbing means is dispersed on an inert support of diatomaceous earth.

19. An apparatus according to claim 14 wherein the sulfuric acid of the second absorbing means is dispersed on an inert support of diatomaceous earth and comprises about 40% of the combined weight of said acid and said support.

20. An apparatus according to claim 14 including the following:

(o) means to maintain the first absorbing means at a temperature of 95°–115° C., (p) means to provide a programmed temperature in the range of −20 to +100° C. for the first, second and third chromatographic separation means, and (q) means to maintain the second absorbing means at a temperature of 100° C.±5° C.

* * * * *